United States Patent [19]

Sagawa et al.

[11] Patent Number: 5,182,390
[45] Date of Patent: Jan. 26, 1993

[54] ISOCYANURIC ACID DERIVATIVE USEFUL AS A LIGHT STABILIZER

[75] Inventors: Seiji Sagawa, Tokyo; Toshio Kano, Sagamihara; Shinichi Yachigo, Toyonaka; Kanako Ida, Ashiya, all of Japan

[73] Assignees: Kyodo Chemical Company Limited, Tokyo, Japan; Sumitomo Chemical Company, Limited, Osaka, Japan

[21] Appl. No.: 783,225

[22] Filed: Oct. 28, 1991

[30] Foreign Application Priority Data

Oct. 29, 1990 [JP] Japan ................................ 2-292559

[51] Int. Cl.$^5$ ........................................ C07D 401/14
[52] U.S. Cl. .................................................... 544/222
[58] Field of Search .......................................... 544/222

[56] References Cited

U.S. PATENT DOCUMENTS 4,393,060 7/1983 Fischer et al. ...................... 544/222

OTHER PUBLICATIONS

Gächter et al., "Taschenbuch der Kunststoff-Additive", Carl Hamser Verlag (1979), pp. 124–135.
Chemical Abstracts, vol. 102, entry 133159e (1985).

*Primary Examiner*—John M. Ford
*Attorney, Agent, or Firm*—Stevens, Davis, Miller & Mosher

[57] ABSTRACT

Tris[2-hydroxy-3-(2,2,6,6-tetramethyl-4-piperidylamino)propyl] isocyanurate is useful as a light stabilizer for organic materials. A composition comprising an organic material and the isocyanurate is stable against light and also excellent in heat resistance. The isocyanurate can be produced by the reaction between tris(2,3-epoxypropyl) isocyanurate and 4-amino-2,2,6,6-tetramethylpiperidine.

2 Claims, No Drawings

ISOCYANURIC ACID DERIVATIVE USEFUL AS A LIGHT STABILIZER

The present invention relates to an isocyanuric acid derivative useful as a light stabilizer for organic materials, as well as its production and use.

In general, various organic materials such as synthetic resins, synthetic rubbers, paints and waxes are easily deteriorated by the action of light. In order to prevent the organic materials from such deterioration, various light stabilizers have hitherto been used. For example, known representative light stabilizers include hindered amine light stabilizers, benzotriazole ultraviolet absorbers, benzophenone ultraviolet absorbers and the like.

One of the objects of the present invention is to provide a compound imparting excellent light stability as well as excellent heat resistance to the organic materials which are blended therewith.

Another object of the invention is to provide a production method of such compound.

A further object of the invention is to provide use of such compound as a light stabilizer for organic materials.

Thus, the present invention provides tris[2-hydroxy-3-(2,2,6,6-tetramethyl-4-piperidylamino)propyl-]isocyanurate which is a novel compound. The isocyanurate is represented by the following formula (I),

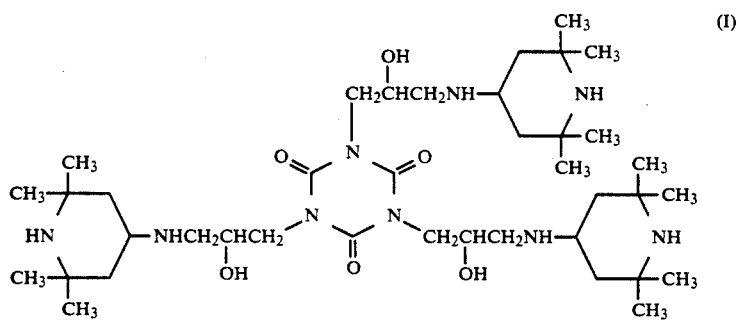

and this compound will sometimes be referred to as "isocyanurate (I)" hereunder.

The present invention also provides a method for producing the isocyanurate (I) by subjecting tris(2,3-epoxypropyl) isocyanurate to a reaction with 4-amino-2,2,6,6-tetramethylpiperidine. The starting tris(2,3-epoxypropyl) isocyanurate is represented by the following formula (II),

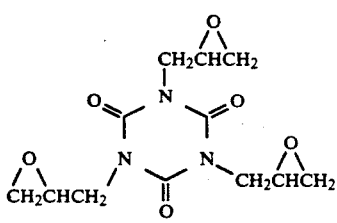

It will sometimes be referred to as "epoxy compound (II)" hereunder. Another starting 4-amino-2,2,6,6-tetramethylpiperidine is represented by the following formula (III),

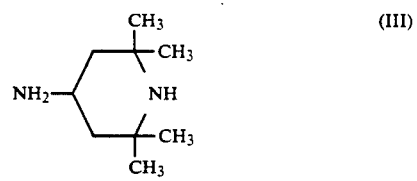

It will sometimes be referred to as "piperidine compound (III)" hereunder.

The present invention further provides a method for stabilizing an organic material liable to be degraded by light, which comprises blending the organic material with a stabilizing amount of the isocyanurate (I), and still further provides a stabilized composition comprising the organic material and the isocyanurate (I).

At the production of the isocyanurate (I) according to the present invention, the reaction between the epoxy compound (II) and the piperidine compound (III) is, in general, carried out by using the piperidine compound (III) in an amount of from about 3 to about 4 moles per mole of the epoxy compound (II), and preferably by blending the epoxy compound (II) and the piperidine compound (III) in a molar ratio of about 1:3. The reaction proceeds, in general, under an atmospheric pressure, and is carried out at a temperature of from about 80° to about 120° C.

The reaction can proceed by admixing the epoxy compound (II) with the piperidine compound (III) and heating the mixture without using a solvent, but can also be conducted in a solvent. In case of using a solvent, the applicable solvent includes, for example, ketone solvents such as acetone, methyl ethyl ketone and methyl isobutyl ketone, and the like.

The isocyanurate (I) of the present invention is effective for stabilizing organic materials, particularly those having a tendency to deteriorate by the action of light. Examples of organic materials which can be stabilized according to the present invention are illustrated below, but they are not limitative to the invention.

(1) Polyethylenes, such as high density polyethylene (HD-PE), low density polyethylene (LD-PE) and linear low density polyethylene (L-LDPE);
(2) Polypropylene;
(3) Methylpentene polymer;
(4) EEA (ethylene/ethyl acrylate copolymer) resin;
(5) Ethylene/vinyl acetate copolymer resin;
(6) Polystyrenes, such as polystyrene, poly(p-methylstyrene) and poly(α-methylstyrene);
(7) AS (acrylonitrile/styrene copolymer) resin;
(8) ABS (acrylonitrile/butadiene/styrene copolymer) resin;

(9) AAS (special acrylic rubber/acrylonitrile/styrene copolymer) resin;
(10) ACS (acrylonitrile/chlorinated polyethylene/styrene copolymer) resin;
(11) Chlorinated polyethylene, polychloroprene and chlorinated rubber;
(12) Poly(vinyl chloride) and poly(vinylidene chloride);
(13) Methacrylic resin;
(14) Ethylene/vinyl alcohol copolymer resin;
(15) Fluororesin;
(16) Polyacetal;
(17) Grafted polyphenylene ether resin and polyphenylene sulfide resin;
(18) Polyurethane;
(19) Polyamide;
(20) Poly(ethylene terephthalate) and poly(butylene terephthalate);
(21) Polycarbonate;
(22) Polyallylate;
(23) Polysulfone, polyether ether ketone and polyether sulfone;
(24) Aromatic polyester resin;
(25) Epoxy resin;
(26) Diallyl phthalate prepolymer;
(27) Silicone resin;
(28) Unsaturated polyester resin;
(29) Acrylic modified benzoguanamine resin;
(30) Benzoguanamine/melamine resin;
(31) Urea resin;
(32) Polybutadiene;
(33) 1,2-Polybutadiene;
(34) Polyisoprene;
(35) Styrene/butadiene copolymer;
(36) Butadiene/acrylonitrile copolymer;
(37) Ethylene/propylene copolymer;
(38) Silicone rubber;
(39) Epichlorohydrin rubber;
(40) Acrylic rubber;
(41) Chlorinated rubber type paints;
(42) Polyester resin paints;
(43) Urethane resin paints;
(44) Epoxy resin paints;
(45) Acrylic resin paints;
(46) Vinyl resin paints;
(47) Aminoalkyd resin paints;
(48) Alkyd resin paints;
(49) Nitrocellulose paints;
(50) Oil paints;
(51) Waxes;
(52) Lubricants of synthetic ester base; and the like.

When the isocyanurate (I) of the invention is applied as a stabilizer for organic materials, its quantity to be blended varies depending on the kinds of the organic materials, but in general, the isocyanurate is preferably incorporated in an amount ranging from about 0.01 to about 2 parts by weight based on 100 parts by weight of the organic material. Its incorporation in an amount of less than 0.01 part by weight is not so sufficient for the stabilizing effect, while its incorporation in an amount of more than 2 parts by weight does not produce any further improvements corresponding to the increased amount and is not economical.

The organic material composition blended with the isocyanurate (I) according to the invention may contain one or more of any other additives when the occasion demands. Such other additives include, for example, antioxidants, hindered amine light stabilizers other than the isocyanurate (I), ultraviolet absorbers, metal deactivators, metal soap, lubricants, nucleating agents, epoxy compounds, plasticizers, flame retardants, antistatic agents, blowing agents, pigments, fluorescent brightening agents, inorganic fillers, organotin stabilizers, organometallic stabilizers, stabilizing auxiliaries and the like.

Preferred examples of the antioxidants to be used in combination with the isocyanurate (I) of the invention are phenolic antioxidants, phosphorus antioxidants and the like.

The phenolic antioxidants include, for example,
octadecyl 3-(3,5-di-t-butyl-4-hydroxyphenyl)propionate,
triethylene glycol bis[3-(3-t-butyl-4-hydroxy-5-methylphenyl)propionate],
3,9-bis[2-(3-(3-t-butyl-4-hydroxy-5-methylphenyl)-propionyloxy)-1,1-dimethylethyl]-2,4,8,10-tetraoxaspiro[5.5]undecane,
pentaerythrityl tetrakis[3-(3,5-di-t-butyl-4-hydroxyphenyl)propionate],
tris(3,5-di-t-butyl-4-hydroxybenzyl) isocyanurate,
1,3,5-trimethyl-2,4,6-tris(3,5-di-t-butyl-4-hydroxybenzyl)benzene,
2,4-bis(n-octylthio)-6-(3,5-di-t-butyl-4-hydroxyanilino)-1,3,5-triazine,
1,6-hexylidene bis[3-(3,5-di-t-butyl-4-hydroxyphenyl)propionate],
2,2'-thiodiethylene bis[3-(3,5-di-t-butyl-4-hydroxyphenyl)propionate],
tris(4-t-butyl-3-hydroxy-2,6-dimethylbenzyl) isocyanurate,
2,4-di-t-amyl-6-[1-(3,5-di-t-amyl-2-hydroxyphenyl)ethyl]phenyl acrylate,
2-t-butyl-6-(3-t-butyl-2-hydroxy-5-methylbenzyl)-4-methylphenyl acrylate,
2,6-di-t-butyl-4-methylphenol,
2,2'-methylenebis(4-methyl-6-t-butylphenol),
4,4'-thiobis(3-methyl-6-t-butylphenol),
4,4'-butylidenebis(3-methyl-6-t-butylphenol),
2,2'-methylenebis(4-ethyl-6-t-butylphenol),
2,2'-methylenebis[6-(1-methylcyclohexyl)-p-cresol],
and the like.

The phosphorus antioxidants include, for example,
tris(nonylphenyl) phosphite,
tris(2,4-di-t-butylphenyl) phosphite,
tetrakis(2,4-di-t-butylphenyl) 4,4'-biphenylene diphosphonite,
bis(2,4-di-t-butylphenyl) pentaerythritol diphosphite,
distearyl pentaerythritol diphosphite,
phenyl diisooctyl phosphite,
phenyl diisodecyl phosphite,
phenyl di(tridecyl) phosphite,
diphenyl isooctyl phosphite,
diphenyl isodecyl phosphite,
diphenyl tridecyl phosphite,
4,4'-isopropylidenebis(phenyl dialkyl phosphite), and the like.

Examples of the ultraviolet absorbers which may be used in combination with the isocyanurate (I) of the invention are benzophenone ultraviolet absorbers, benzotriazole ultraviolet absorbers and the like.

The benzophenone ultraviolet absorbers include, for example,
2-hydroxy-4-methoxybenzophenone,
2-hydroxy-4-octoxybenzophenone,
2,2'-dihydroxy-4-methoxybenzophenone,
bis(5-benzoyl-4-hydroxy-2-methoxyphenyl)methane,
2,2',4,4'-tetrahydroxybenzophenone, and the like.

The benzotriazole ultraviolet absorbers include, for example,
2-(2-hydroxy-5-methylphenyl)benzotriazole,
2-[2-hydroxy-3-(3,4,5,6-tetrahydrophthalimidemethyl)-5-methylphenyl]benzotriazole,
2-(3-t-butyl-2-hydroxy-5-methylphenyl)-5-chlorobenzotriazole,
2-(3,5-di-t-butyl-2-hydroxyphenyl)benzotriazole,
2-(2-hydroxy-5-t-octylphenyl)benzotriazole,
2-(3,5-di-t-amyl-2-hydroxyphenyl)benzotriazole,
2-[2-hydroxy-3,5-bis(α,α-dimethylbenzyl)phenyl]-2H-benzotriazole,
2-(3,5-di-t-butyl-2-hydroxyphenyl)-5-chlorobenzotriazole,
2,2'-methylenebis[6-(2H-benzotriazol-2-yl)-4-(1,1,3,3-tetramethylbutyl)phenol],
a condensation product of poly(3-11)(ethylene glycol) with methyl 3-[3-(2H-benzotriazol-2-yl)-5-t-butyl-4-hydroxyphenyl]propionate,
2-ethylhexyl 3-[3-t-butyl-5-(5-chloro-2H-benzotriazol-2-yl)-4-hydroxyphenyl]propionate,
octyl 3-[3-t-butyl-5-(5-chloro-2H-benzotriazol-2-yl)-4-hydroxyphenyl]propionate,
methyl 3-[3-t-butyl-5-(5-chloro-2H-benzotriazol-2-yl)-4-hydroxyphenyl]propionate,
3-[3-t-butyl-5-(5-chloro-2H-benzotriazol-2-yl)-4-hydroxyphenyl]propionic acid,
2,2'-methylenebis[4-t-butyl-6-(2H-benzotriazol-2-yl)phenol, and the like.

Other hindered amine light stabilizers which can be used in combination with the isocyanurate (I) of the invention include, for example,
bis(2,2,6,6-tetramethyl-4-piperidyl) sebacate,
bis(1,2,2,6,6-pentamethyl-4-piperidyl) sebacate,
poly[{6-(1,1,3,3-tetramethylbutyl)imino-1,3,5-triazin-2,4-diyl}{(2,2,6,6-tetramethyl-4-piperidyl)imino}-hexamethylene{(2,2,6,6-tetramethyl-4-piperidyl)-imino}],
poly[(6-morpholino-1,3,5-triazin-2,4-diyl)((2,2,6,6-tetramethyl-4-piperidyl)imino}hexamethylene-{(2,2,6,6-tetramethyl-4-piperidyl)imino}],
a polycondensation product of dimethyl succinate with 1-(2-hydroxyethyl)-4-hydroxy-2,2,6,6-tetramethylpiperidine, and the like.

The isocyanurate (I) of the present invention can be incorporated as a stabilizer into an organic material by using any known apparatus and in accordance with any known operation procedure. For example, when the organic material is a solid polymer, the polymer may be blended with the stabilizer in a dry state, and otherwise may be blended with a solution, suspension or emulsion of the stabilizer. Besides, when the organic material is a polymer, the stabilizer can also be added thereto at the production procedure of the polymer. In this case, the stabilizer may be added directly into a polymerizing reaction solution during or after the polymerization, and also may be added in the state of a solution, suspension or emulsion. When the organic material is a liquid such as oil, the stabilizer may be directly added to the liquid to admix them, and besides, may be made as a concentrated solution in oil or the like to be added to the liquid organic material.

Tris[2-hydroxy-3-(2,2,6,6-tetramethyl-4-piperidylamino)propyl] isocyanurate of the present invention exhibits excellent light stabilizing effect as well as high performance in improving heat resistance, when it is incorporated into organic materials.

The present invention will be explained in more detail with reference to the following examples, which are only illustrative but not limitative to the invention. In the examples, percentages and parts are by weight unless otherwise indicated.

EXAMPLE 1

Production of tris[2-hydroxy-3-(2,2,6,6-tetramethyl-4-piperidylamino)propyl]isocyanurate (I)

A reaction vessel equipped with a thermometer and a stirrer were charged with 29.7 g (0.1 mole) of tris(2,3-epoxypropyl) isocyanurate and 47.5 g (0.3 mole) of 4-amino-2,2,6,6-tetramethylpiperidine, and the mixture was gradually heated with stirring in a hot water bath. An exothermic phenomenon was observed at about 80° C. The mixture was further heated to 100°±5° C., and kept at that temperature for about 2 hours. Thereafter the mixture was cooled to obtain 74.5 g of tris[2-hydroxy-3-(2,2,6,6-tetramethyl-4-piperidylamino)-propyl] isocyanurate (I) as white powder; the yield being 97.4%.

Melting point: 55°–60° C.

| Elemental analysis: $C_{39}H_{75}N_9O_6$ | | |
| --- | --- | --- |
| | Found | (Calculated) |
| C: | 61.7% | (61.2%) |
| H: | 9.7% | (9.8%) |
| N: | 15.6% | (16.5%) |
| O: | 13.0% | (12.5%) |

Mass spectrometry (FD-MS): M/Z 767 (M+1)

The isocyanurate (I) obtained in this Example and the compounds listed below were used to carry out the stability tests for organic materials in Example 2 and following.

HALS-1: Bis(2,2,6,6-tetramethyl-4-piperidyl) sebacate
HALS-2: Poly[(6-morpholino-1,3,5-triazin-2,4-diyl)-{(2,2,6,6-tetramethyl-4-piperidyl)imino}-hexamethylene{(2,2,6,6-tetramethyl-4-piperidyl)-imino}]
HALS-3 A polycondensation product of dimethyl succinate with 1-(2-hydroxyethyl)-4-hydroxy-2,2,6,6-tetramethylpiperidine
UVA-1 2-(3-t-butyl-2-hydroxy-5-methylphenyl)-5-chlorobenzotriazole

EXAMPLE 2

Unstabilized polypropylene was dry-blended in accordance with the following formulation:

| [Compounding formulation] | |
| --- | --- |
| Unstabilized polypropylene | 100 parts |
| Calcium stearate | 0.05 part |
| Pentaerythrityl tetrakis[3-(3,5-di-t-butyl-4-hydroxyphenyl)propionate] | 0.2 part |
| Tris(2,4-di-t-butylphenyl) phosphite | 0.05 part |
| Test compoud | as in Table 1 |

Each blend was kneaded under melting at 230° C. using a uniaxial 30 mm calibered extruder and pelletized. The pellets obtained were formed to a sheet of 1 mm thickness using a one-ounce injection molding machine.

The resulting sheet was used as a test piece, and each test piece was set in a sunshine weather-O-meter having a light source of carbon arc, and exposed to light under a spraying cycle of 120 minutes and a spraying time of 18 minutes. The surface of the test piece was inspected with a microscope of 25 magnifications at an interval of 60 hours. The weathering resistance was evaluated by the time when a crack appeared on the surface.

The results are shown in Table 1.

TABLE 1

| Run No. | Invention | | Comparison | | |
|---|---|---|---|---|---|
| | 1-1 | 1-2 | 1-3 | 1-4 | 1-5 |
| Test compound (part) | | | | | |
| (I) | 0.1 | 0.2 | | | |
| HALS-1 | | | none | 0.2 | |
| UVA-1 | | | | | 0.2 |
| Weathering resistance (hours) | 480 | 720 | 240 | 540 | 360 | paper to start turning blue caused by dehydrochlorination of the poly(vinyl chloride). Since the poly(vinyl chloride) resin evolves hydrogen chloride gas with the degradation, the longer the time required for the Congo Red test paper to start turning blue (or to change into acidity), the higher the heat resistance.

On the other hand, the same three films were pressed at 165° C., and the resulting press sheet was put in EYE SUPER UV TESTER (Dainippon Plastics Co., Ltd., Type SUV-W-1) having a setting temperature of 63° C. to be exposed to ultraviolet for 80 hours. The light stability was evaluated by the film hue after the exposure. The lower the discoloration after exposure for 80 hours, the higher the light stability.

The results of each test are shown in Table 2.

TABLE 2

| Run No. | Invention | | Comparison | | | | | | |
|---|---|---|---|---|---|---|---|---|---|
| | 2-1 | 2-2 | 2-3 | 2-4 | 2-5 | 2-6 | 2-7 | 2-8 | 2-9 |
| Test compound (part) | | | | | | | | | |
| (I) | 0.05 | 0.1 | none | | | | | | |
| HALS-1 | | | | 0.05 | 0.1 | | | | |
| HALS-2 | | | | | | 0.05 | 0.1 | | |
| HALS-3 | | | | | | | | 0.05 | 0.1 |
| Heat resistance | | | | | | | | | |
| Geer oven test (min.) | 90 | 100 | 60 | 70 | 80 | 80 | 90 | 70 | 80 |
| Congo Red test (sec.) | 3774 | 4352 | 2918 | 3184 | 3622 | 3499 | 3932 | 3089 | 3144 |
| Light stability | | | | | | | | | |
| Hue after 80 hours exposure in UV tester | Pale yellowish brown | Pale yellow | Brown | Yellowish brown | Pale yellowish brown | Yellowish brown | Pale yellowish brown | Yellowish brown | Pale yellowish brown |

EXAMPLE 3

Poly(vinyl chloride) resin was dry-blended in accordance with the following formulation:

| [Compounding formulation] | |
|---|---|
| Poly(vinyl chloride) | 100 parts |
| Dioctyl phthalate | 40 parts |
| Epoxy soybean oil | 2 parts |
| 4,4'-isopropylidenebis(phenyl dialkyl phosphite) | 1 part |
| Barium stearate | 0.6 part |
| Zinc stearate | 0.4 part |
| Test compound | as in Table 2 |

Each blend was kneaded for 5 minutes using 6 inch test rolls to prepare a film of 0.2 mm thickness.

The film obtained was aged in a Geer oven to determine the time required to turn black. The longer the time required to turn black, the higher the heat resistance.

Separately, the same film was chopped to small pieces, and the chopped pieces were placed in a test tube. Congo Red test paper dampened with glycerin was held in the test tube with absorbent cotton, and the test tube was sealed and dipped in an oil bath of 185° C. to determine the time required for the Congo Red test

EXAMPLE 4

Poly(vinyl chloride) resin was dry-blended in accordance with the following formulation:

| [Compounding formulation] | |
|---|---|
| Poly(vinyl chloride) | 100 parts |
| Dioctyl phthalate | 60 parts |
| Higher fatty acid ester type lubricant (LX-40A-2, produced by Kyodo Chemical Co., Ltd.) | 0.2 part |
| Monobutyltin tris(octyloxycarbonylmethylenemercaptide) | 0.6 part |
| Test compound | as in Table 3 |

Each blend was formed to a film of 0.2 mm thickness in the same manner as in Example 3, and the resulting film was subjected to the same Congo Red test as in Example 3. The results are shown in Table 3.

TABLE 3

| Run No. | Invention | | Comparison | | | | | | |
|---|---|---|---|---|---|---|---|---|---|
| | 3-1 | 3-2 | 3-3 | 3-4 | 3-5 | 3-6 | 3-7 | 3-8 | 3-9 |
| Test compound (part) | | | | | | | | | |
| (I) | 0.1 | 0.5 | none | | | | | | |
| HALS-1 | | | | 0.1 | 0.5 | | | | |
| HALS-2 | | | | | | 0.1 | 0.5 | | |
| HALS-3 | | | | | | | | 0.1 | 0.5 |
| Heat resistance | | | | | | | | | |
| Congo Red test (sec.) | 2550 | 3060 | 2160 | 2055 | 2250 | 2350 | 2565 | 2265 | 2550 |

What is claimed is:

1. Tris[2-hydroxy-3-(2,2,6,6-tetramethyl-4-piperidylamino)propyl] isocyanurate.

2. A method for producing tris[2-hydroxy-3-(2,2,6,6-tetramethyl-4-piperidylamino)propyl] isocyanurate, which comprises subjecting tris(2,3-epoxypropyl) isocyanurate to a reaction with 4-amino-2,2,6,6-tetramethylpiperidine.

* * * * *